US00RE43714E

(19) United States
(12) Reissued Patent
Nadler et al.

(10) Patent Number: US RE43,714 E
(45) Date of Reissued Patent: Oct. 2, 2012

(54) PREPARATION FOR REPAIRING CARTILAGE DEFECTS OR CARTILAGE/BONE DEFECTS IN HUMAN OR ANIMAL JOINTS

(75) Inventors: Daniel Nadler, Hettlingen (CH); Pedro Bittmann, Zürich (CH); Margarete K. Akens, Toronto (CA); Brigitte Von Rechenberg, Zürich (CH); Jorg Auer, Lenzburg (CH)

(73) Assignee: Zimmer Orthobiologics, Inc., Austin, TX (US)

(21) Appl. No.: 11/705,575

(22) Filed: Feb. 12, 2007

Related U.S. Patent Documents

Reissue of:

(64) Patent No.: 6,858,042
Issued: Feb. 22, 2005
Appl. No.: 10/149,853
PCT Filed: Dec. 12, 2000
PCT No.: PCT/CH00/00659
§ 371 (c)(1),
(2), (4) Date: Oct. 17, 2002
PCT Pub. No.: WO01/43667
PCT Pub. Date: Jun. 21, 2001

(30) Foreign Application Priority Data

Dec. 15, 1999 (CH) ..... 2296/99

(51) Int. Cl.
*A61F 2/02* (2006.01)

(52) U.S. Cl. ..... 623/11.11; 623/23.75; 424/423

(58) Field of Classification Search ..... 623/11.11, 623/18.11, 23.73, 23.72, 23.75, 16.11, 23.74, 623/14.12, 23.48, 23.47, 23.39; 606/80; 424/484, 423, 424; 435/297.1, 297.5, 180
See application file for complete search history.

(56) References Cited

U.S. PATENT DOCUMENTS 1,703,154 A 2/1929 Lanzkron
(Continued)

FOREIGN PATENT DOCUMENTS

AU 700349 1/1997
(Continued)

OTHER PUBLICATIONS

Bakay et al., *International Orthopaedics* 20:370-372 (1996).
(Continued)

*Primary Examiner* — Pedro Philogene
(74) *Attorney, Agent, or Firm* — Schwegman Lundberg & Woessner, P.A.

(57) ABSTRACT

Repairs of cartilage defects or of cartilage/bone defects in human or animal joints with the help of devices including a bone part (1), a cartilage layer (2) and a subchondral bone plate (4) or an imitation of such a plate in the transition region between the cartilage layer (2) and the bone part (1). After implantation, the bone part (4) is resorbed and is replaced by reparative tissue only after being essentially totally resorbed. In a critical phase of the healing process, a mechanically inferior cyst is located in the place of the implanted bone part (1). In order to prevent the cartilage layer (2) from sinking into the cyst space during this critical phase of the healing process the device has a top part (11). and a bottom part (12), wherein the top part (11) consists essentially of the cartilage layer (2) and the subchondral bone plate (4) and the bottom part (12) corresponds essentially to the bone part (1) and wherein the top part (11) parallel to the subchondral bone plate (4) has a larger diameter than the bottom part (12). After implantation in a suitable opening or bore (20), the cartilage layer (2) and the subchondral bone plate (4) are supported not only on the bone part (1) but also on native bone tissue having a loading capacity not changing during the healing process. Therefore, the implanted cartilage layer cannot sink during the healing process.

34 Claims, 6 Drawing Sheets

U.S. PATENT DOCUMENTS

| | | | | |
|---|---|---|---|---|
| 3,971,273 | A | 7/1976 | Peters et al. | |
| 4,589,206 | A | 5/1986 | Marcoux | |
| 4,627,853 | A | 12/1986 | Campbell et al. | 623/16 |
| 4,932,973 | A | 6/1990 | Gendler | 623/16 |
| 5,002,583 | A | 3/1991 | Pitaru et al. | 623/66 |
| 5,112,354 | A | 5/1992 | Sires | |
| 5,115,704 | A | 5/1992 | Hyman | |
| 5,152,791 | A | 10/1992 | Hakamatsuka et al. | 623/16 |
| 5,211,661 | A | 5/1993 | Shinjou et al. | 623/16 |
| 5,320,115 | A | 6/1994 | Kenna | 128/898 |
| 5,320,626 | A | 6/1994 | Schmieding | |
| 5,370,692 | A | 12/1994 | Fink et al. | |
| 5,496,326 | A | 3/1996 | Johnson | |
| 5,591,234 | A | 1/1997 | Kirsch | 623/16 |
| 5,603,716 | A | 2/1997 | Morgan et al. | |
| 5,632,745 | A | 5/1997 | Schwartz | 606/75 |
| 5,632,747 | A | 5/1997 | Scarborough et al. | 606/79 |
| 5,718,707 | A | 2/1998 | Mikhail | 606/94 |
| 5,741,685 | A | 4/1998 | Vacanti | 435/182 |
| 5,769,899 | A | 6/1998 | Schwartz et al. | 623/18 |
| 5,782,835 | A | 7/1998 | Hart et al. | 606/79 |
| 5,785,522 | A | 7/1998 | Bergstrom et al. | |
| 5,817,153 | A | 10/1998 | Pendl et al. | 8/94.11 |
| 5,853,746 | A | 12/1998 | Hunziker | 424/426 |
| 5,876,452 | A * | 3/1999 | Athanasiou et al. | 623/23.72 |
| 5,881,733 | A | 3/1999 | Stone | 128/898 |
| 5,885,293 | A | 3/1999 | McDevitt | |
| 5,919,196 | A | 7/1999 | Bobic et al. | 606/86 |
| 6,013,853 | A | 1/2000 | Athanasiou et al. | 623/11 |
| 6,017,348 | A * | 1/2000 | Hart et al. | 606/79 |
| 6,025,538 | A | 2/2000 | Yaccarino, III | 623/16 |
| 6,027,743 | A | 2/2000 | Khouri et al. | 424/423 |
| 6,110,178 | A | 8/2000 | Zech et al. | 606/96 |
| 6,110,482 | A | 8/2000 | Khouri et al. | 424/423 |
| 6,123,731 | A | 9/2000 | Boyce et al. | 623/23.63 |
| 6,146,385 | A | 11/2000 | Torrie et al. | 606/96 |
| 6,179,871 | B1 | 1/2001 | Halpern | 623/11.11 |
| 6,193,722 | B1 | 2/2001 | Zech et al. | |
| 6,235,035 | B1 | 5/2001 | Boukhris | |
| 6,242,247 | B1 * | 6/2001 | Rieser et al. | 435/297.1 |
| 6,251,143 | B1 * | 6/2001 | Schwartz et al. | 623/23.72 |
| 6,358,253 | B1 | 3/2002 | Torrie et al. | 606/96 |
| 6,440,141 | B1 | 8/2002 | Philippon | 606/99 |
| 6,459,948 | B1 | 10/2002 | Ateshian et al. | |
| 6,468,314 | B2 | 10/2002 | Schwartz et al. | 623/23.72 |
| 6,488,033 | B1 | 12/2002 | Cerundolo | 128/898 |
| 6,520,964 | B2 | 2/2003 | Tallarida et al. | |
| 6,530,928 | B1 | 3/2003 | Frei et al. | |
| 6,569,200 | B2 | 5/2003 | Wolfinbarger, Jr. et al. | 623/13.11 |
| 6,591,581 | B2 | 7/2003 | Schmieding | |
| 6,592,588 | B1 | 7/2003 | Bobic et al. | 606/79 |
| 6,626,945 | B2 | 9/2003 | Simon et al. | 623/17.19 |
| 6,626,950 | B2 | 9/2003 | Brown et al. | 623/23.72 |
| 6,632,246 | B1 | 10/2003 | Simon et al. | 623/14.12 |
| 6,679,917 | B2 | 1/2004 | Ek | |
| 6,699,252 | B2 | 3/2004 | Farr, II et al. | 606/79 |
| 6,727,224 | B1 | 4/2004 | Zhang et al. | 514/12 |
| 6,793,676 | B2 | 9/2004 | Plouhar et al. | 623/14.12 |
| 6,852,114 | B2 | 2/2005 | Cerundolo | 606/80 |
| 6,852,125 | B2 | 2/2005 | Simon et al. | 623/16.11 |
| 6,858,042 | B2 | 2/2005 | Nadler et al. | |
| 6,988,015 | B1 | 1/2006 | Schopf et al. | |
| 7,029,479 | B2 | 4/2006 | Tallarida et al. | |
| 7,037,339 | B2 | 5/2006 | Houfburg | |
| 7,291,149 | B1 | 11/2007 | Michelson | |
| 2002/0013627 | A1 | 1/2002 | Geistlich et al. | 623/23.63 |
| 2002/0082704 | A1 | 6/2002 | Cerundolo | 623/20.35 |
| 2003/0036801 | A1 | 2/2003 | Schwartz et al. | 623/23.63 |
| 2003/0064090 | A1 | 4/2003 | Khouri et al. | 424/426 |
| 2003/0135209 | A1 | 7/2003 | Seedhom et al. | 606/60 |
| 2003/0216669 | A1 | 11/2003 | Lang et al. | 600/587 |
| 2003/0220700 | A1 | 11/2003 | Hammer et al. | 623/23.58 |
| 2003/0225459 | A1 | 12/2003 | Hammer et al. | 623/23.72 |
| 2003/0229400 | A1 | 12/2003 | Masuda et al. | 623/23.63 |
| 2004/0034359 | A1 | 2/2004 | Schmieding et al. | 606/86 |
| 2004/0059425 | A1 | 3/2004 | Schmieding | 623/20.16 |
| 2004/0073223 | A1 | 4/2004 | Burkinshaw | 606/79 |
| 2004/0147932 | A1 | 7/2004 | Burkinshaw et al. | 606/79 |
| 2004/0176771 | A1 | 9/2004 | Schmieding | 606/80 |
| 2004/0192605 | A1 | 9/2004 | Zhang et al. | 514/12 |
| 2004/0230303 | A1 | 11/2004 | Gomes et al. | 623/16.11 |
| 2005/0043813 | A1 | 2/2005 | Kusanagi et al. | 623/23.58 |
| 2005/0043814 | A1 | 2/2005 | Kusanagi et al. | 623/23.58 |
| 2005/0064042 | A1 | 3/2005 | Vunjak-Novakovic et al. | 424/549 |
| 2005/0089544 | A1 | 4/2005 | Khouri et al. | 424/426 |
| 2005/0209705 | A1 | 9/2005 | Niederauer et al. | 623/23.63 |
| 2005/0222687 | A1 | 10/2005 | Vunjak-Novakovic et al. | 623/23.63 |
| 2005/0251268 | A1 | 11/2005 | Truncale | 623/23.63 |
| 2006/0024380 | A1 | 2/2006 | Abraham et al. | |
| 2006/0060209 | A1 | 3/2006 | Shepard | 128/898 |
| 2006/0083729 | A1 | 4/2006 | Kusanagi et al. | 424/94.1 |
| 2006/0178748 | A1 | 8/2006 | Dinger, III et al. | 623/18.11 |
| 2006/0195188 | A1 | 8/2006 | O'Driscoll et al. | 623/14.12 |
| 2006/0247790 | A1 | 11/2006 | McKay | |
| 2007/0093896 | A1 | 4/2007 | Malinin | 623/14.12 |
| 2007/0135917 | A1 | 6/2007 | Malinin | 623/16.11 |
| 2007/0135918 | A1 | 6/2007 | Malinin | 623/16.11 |
| 2007/0135928 | A1 | 6/2007 | Malinin | 623/23.63 |
| 2007/0276506 | A1 | 11/2007 | Troxel | |
| 2007/0299517 | A1 | 12/2007 | Davisson et al. | |
| 2008/0027447 | A1 | 1/2008 | Gil et al. | |
| 2008/0051812 | A1 | 2/2008 | Schmitz et al. | |
| 2012/0053588 | A1 | 3/2012 | Lozier et al. | |
| 2012/0053642 | A1 | 3/2012 | Lozier et al. | |

FOREIGN PATENT DOCUMENTS

| | | | | |
|---|---|---|---|---|
| AU | 717552 | | 3/1998 | |
| DE | 29 33 174 | A | 4/1980 | |
| DE | 43 17 448 | A | 11/1994 | |
| DE | 4317448 | * | 11/1994 | 623/11.11 |
| DE | 195 03 504 | A | 3/1996 | |
| EP | 0 493 698 | A | 7/1992 | |
| EP | 0 768 332 | A | 4/1997 | |
| EP | 0768332 | * | 4/1997 | 623/11.11 |
| EP | 0 815 809 | A2 | 1/1998 | |
| EP | 1 452 150 | A1 | 1/2004 | |
| EP | 0 824 893 | B1 | 11/2005 | |
| EP | 1 234 552 | B1 | 8/2006 | |
| FR | 2 860 423 | | 4/2005 | |
| GB | 2 175 506 | A | 12/1986 | |
| WO | WO93/15694 | | 8/1993 | |
| WO | WO94/26211 | | 11/1994 | |
| WO | WO96/24302 | | 8/1996 | |
| WO | WO96/24310 | | 8/1996 | |
| WO | WO96/27333 | | 9/1996 | |
| WO | WO96/34955 | | 11/1996 | |
| WO | WO97/46665 | | 12/1997 | |
| WO | WO98/34569 | | 8/1998 | |
| WO | WO9834569 | A1 | 8/1998 | |
| WO | WO98/56317 | | 12/1998 | |
| WO | WO99/21497 | | 5/1999 | |
| WO | WO9921497 | | 5/1999 | |
| WO | WO01/05336 | | 1/2001 | |
| WO | WO01/30276 | | 5/2001 | |
| WO | WO01/43667 | | 6/2001 | |
| WO | WO2004/075940 | | 9/2004 | |
| WO | WO2004/103224 | | 12/2004 | |
| WO | WO2005/038016 | | 4/2005 | |
| WO | WO2005/092208 | | 10/2005 | |
| WO | WO2006/026981 | | 3/2006 | |
| WO | WO2006/092718 | | 9/2006 | |

OTHER PUBLICATIONS

Bakay et al., *International Orthopaedics* 22:277-281 (1998).

Gross, "Use of Fresh Osteochondral Allografts to Replace Traumatic Joint Defects," pp. 67-82, *Allografts in Orthopaedic Practice* (Zitrom and Gross, eds., 1992).

Delloye et al., *Acta Orthopaedica Belgica* 57:75-83 (1991).

Czitrom et al., *Clinical Orthopaedics and Related Research,* No. 208, pp. 141-145 (Jul. 1986).

Flynn et al., *Clinical Orthopaedics and Related Research,* No. 303, pp. 38-43 (Jun. 1994).

Garrett, *Clinical Orthopaedics and Related Research,* No. 303, pp. 33-37 (Jun. 1994).
Kawamura et al., *Clinical Orthopaedics and Related Research,* No. 235, pp. 302-310 (Oct. 1988).
Locht et al., *The Journal of Bone and Joint Surgery* 66-A:328-335 (Mar. 1984).
Mahomed et al., *Orthopedics* 15:1191-1199 (Oct. 1992).
McDermott et al., *Clinical Orthopaedics and Related Research,* No. 197, pp. 96-102 (Jul.-Aug. 1985).
Meyers et al., *The Journal of Bone and Joint Surgery* 71-A:704-713 (Jun. 1989).
Stevenson et al., *The Journal of Bone and Joint Surgery* 71-A:1297-1307 (Oct. 1989).
Pollok et al., *Pediatr. Surg. Int.* 15:164-167 (1999).
Pollok et al., *Transplantation Proceedings* 29:2131-2133 (1997).
Baragi et al., *Osteoarthritis and Cartilage* 5:275-282 (1997).
Cornell et al., *Nature* 387:580-583 (Jun. 1997).
Csönge et al., *Cell and Tissue Banking* 3:151-159 (2002).
Csönge et al., *Cell and Tissue Banking* 3:161-168 (2002).
Marco et al., *International Orthopaedics* 17:104-108 (1993).
Akens et al., *BMC Musculoskeletal Disorders* 2:9 (2001).
Bodo et al., *Acta Veterinaria Hungarica* 48(3):343-354 (2000).
Burba et al., *Journal of Investigative Surgery* 5:343-359 (1992).
Hangody et al., *Autogenous Osteochondral Mosaicplasty* 5(3):175-181 (May/Jun. 1997).
Hetherington et al., *BMC Musculoskeletal Disorders* 6:36 (2005).
Hetherington et al., *The Journal of Foot & Ankle Surgery* 46(4):223-229 (Jul./Aug. 2007).
von Rechenberg et al., *OsteoArthritis and Cartilage* 11:265-277 (2003).
von Rechenberg et al., *Vet Comp Orthop Traumatol* 3:147-156 (2006).
von Rechenberg et al., *OsteoArthritis and Cartilage* 12:201-216 (2004).
U.S. Appl. No. 60/024,045, filed Aug. 16, 1996, Reinhold, Schmieding.
Aichroth, et al, "Biological and Mechanical Problems of Osteoarticular Allografting: The Relation to Clinical Organ Transplantation," The Journal of the Western Pacific Orthopaedic Association, 1971, pp. 25-70, vol. VIII, No. 2, London, England.
Akens, et al, "In-vitro and in-vivo studies of osteochondral transplants pretreated with photo-oxidation," Ph.D. Thesis, 2002, pp. 1-100, Ph.D. Program of the Veterinary Faculties of Zurich and Bern.
Bakay, et al., "The alternatives of the application of human lyophilized spongiosa and bone-matrix gelatin," Orvosi Hetilap, 1995, pp. 1891-1896, vol. 136, No. 35, Budapest (Original and Translation enclosed).
Barber, et al., "COR Osteochondral Repair System," Osteobiologics, Inc., 2006, DePuy Mitek, USA.
Beaver, et al., "Fresh Osteochondral Allografts for Post-Traumatic Defects in the Knee," The Journal of Bone and Joint Surgery, 1992, pp. 105-110, vol. 74-B, No. 1, Britain (UK).
Bos, et al., "Immune responses of rats to frozen bone allografts," The Journal of Bone & Joint Surgery, 1983, pp. 239-246, vol. 65, Needham, MA, USA.
Brooks, et al., "Immunological Factors in Homogenous Bone Transplantation: IV. The Effect of Various Methods of Preparation and Irradiation on Antingenicity," The Journal of Bone & Joint Surgery, 1963, pp. 1617-1626, vol. 45, Needham, MA, USA.
Bugbee, et al., "Osteochondral Allograft Transplantation," Complex Topics in Knee Surgery, 1999, pp. 67-75, vol. 18, No. 1, California, USA.
Bugbee, William D., Fresh Osteochondral Allografts, Seminars in Arthroplasty, 2000, pp. 221-226, vol. 11, No. 4, W.B. Saunders Company, San Diego, CA, USA.
Chalmers, J., "Transplantation immunity in bone homografting," The Journal of Bone & Joint Surgery, 1959, pp. 160-179, vol. 41B, No. 1, London, England.
Chu, et al., Articular Cartilage Transplantation—Clinical Results in the Knee, Clinical Orthopaedics and Related Research Journal, 1999, pp. 159-168, No. 360, Lippincott Williams & Watkins, Inc., USA.
Convery, et al., "Fresh osteochondral allografting of the femoral condyle," Clinical Orthopaedics and Related Research, 1991, pp. 139-145, No. 273, San Diego, CA, USA.
Convery, et al., "Long-term survival of chondrocytes in an osteochondral articular cartilage allograft. A Case Report," The Journal of Bone & Joint Surgery, 1996, pp. 1082-1087, vol. 78, Needham, MA, USA.
Convery, et al., "The operative technique of fresh osteochondral allografting of the knee," Operative Techniques in Orthopaedics, 1997, pp. 340-344, vol. 7, No. 4, W.B. Saunders Company, San Diego, CA, USA.
Desjardins, et al., "Incorporation of Fresh and Cryopreserved Bone in Osteochondral Autografts in the Horse," Veterinary Surgery, 1991, pp. 446-452, vol. 20, No. 6, Ontario, Canada.
Donald, Paul J., "Cartilage Grafting in Facial Reconstruction with Special Consideration of Irradiated Grafts"*\, Laryngoscope, 1986, pp. 786-806, vol. 96, Sacramento, CA, USA.
Elves, et al., "A Study of the Humoral Immune Response to Osteoarticular Allografts in the Sheep," Clin. exp. Immunol., 1974, pp. 497-508, vol. 17, Middlesex, UK.
Friedlaender, et al., "Studies on the antigenicity of bone. I. Freeze-dried and deep-frozen bone allografts in rabbits," The Journal of Bone & Joint Surgery, 1976, pp. 854-858, vol. 58, Needham, MA, USA.
Friedlaender, Gary E., "Immune Responses to Osteochondral Allografts," Clinical Orthopaedics and Related Research, 1983, pp. 58-68, No. 174, J.B. Lippincott Co., USA.
Garrett, John C., "Fresh Osteochondral Allografts for Treatment of Articular Defects in Osteochondritis Dissecans of the Lateral Femoral Condyle in Adults," Clinical Orthopaedics and Related Research, 1994, pp. 33037, No. 303, J. B. Lippincott Company, USA.
Garrett, John C., M.D., "Osteochondral Allografts for Reconstruction of Articular Defects of the Knee," AAOS Instructional Course Lectures, 1998, pp. 517-522, vol. 47, USA.
Ghazavi, et al., "Fresh Osteochondral Allografts for Post-Traumatic Osteochondral Defects of the Knee," Journal of Bone & Joint Surgery, 1997, pp. 1008-1013, vol. 79-B, No. 6, Toronto, Canada.
Gould, Nathaniel, "Trephining Your Way," Orthopedic Clinics of North America, 1973, pp. 157-164, vol. 4, No. 1, Brockton, MA, USA.
Gross, et al., "Reconstruction of Skeletal Deficits at the Knee," Climical Orthopaedics and Related Research, 1983, pp. 96-106, No. 174, J.B. Lippincott Co., Philadelphia, PA, USA.
Hetherington, et al., "Immunologic testing for xeno-derived osteocartilagenous grafts," ICRS, 2002, USA.
Hurtig, M.B., "Experimental use of small osteochondral grafts for resurfacing the equine third carpal bone," Equine Orthopaedics, 1988, pp. 23-27, Supp. 6, England.
Hurtig, et al., "Surgical and analytical techniques for articular cartilage transplantation," Veterinary Surgery The Official Journal of The American College of Veterinary Surgeons, Inc., 1992, p. 394, vol. 21, No. 5, J.B. Lippincott Company, Philadelphia, PA, USA.
Hurtig, et al, "Osteochondral Dowel Transplantation for Repair of Focal Defects in the Knee: An Outcome Study Using an Ovine Model," Veterinary Surgery, 1998, pp. 5-16, vol. 27, Alberta, Canada.
Jakob, et al., "Isolated articular cartilage lesion: repair or regeneration," Osteoarthritis and Cartilage Journal of the OsteoArthritis Research Society International, 2001, pp. S3-S5, vol. 9, Supplement A, www.idealibrary.com.
Jakob, et al., "Autologous Osteochondral Grafting in the Knee: Indication, Results, and Reflections," Clinical Orthopaedics and Related Research, 2002, pp. 170-184, No. 401, Lippincott Williams & Wilkins, Inc., USA.
Jamali, et al., "Donor cell survival in a fresh osteochondral allograft at twenty-nine years," The Journal of Bone & Joint Surgery, 2007, pp. 166-169, vol. 89, Needham, MA, USA.
Jimenez, et al., "Experimental Studies onthe Fate of Transplanted Articular Cartilage," Osteochondral Allografts, Biology, Banking and Clinical Applications, 1983, pp. 73-79, Little, Brown & Co., Boston, USA.
Kamijou, et al., "Effects of Osteocytes on Osteoinduction i nthe Autogenous Rib Graft in the Rat Mandible," Bone, 1994, pp. 629-637, vol. 15, No. 6, Elsevier Science Ltd., USA.

Kelley, et al., "Chondrocyte repopulation of allograft cartilage: A preliminary investigation and strategy for developing cartilage matrices for reconstruction," Otolaryngology-Head and Neck Surgery, 2002, pp. 265-270, vol. 127, No. 4, Washington, DC, USA.
Kluger, et al, "Removal of the surface layers of human cortical bone allografts restores in vitro osteoclast function reduced by processing and frozen storage," Bone, 2003, pp. 291-296, vol. 32, Elsevier Science, USA.
Kwan, et al., "Histological and Biomechanical Assessment of Articular Cartilage from Stored Osteochondral Shell Allografts," Journal of Orthopaedic Research, 1989, pp. 637-644, vol. 7, No. 5, USA.
Lexer, E., "Joint transplantation," Clinical Orthopaedics and Related Research, 1985, pp. 4-10, No. 197, USA.
Malinin, et al., Banking of Massive Osteoarticular and Intercalary Bone Allografts—12 Years' Experience, Clinical Orthopaedics and Related Research, 1985, pp. 44-57, No. 197. Miami, FL, USA.
Malinin, et al., "Cryopreservation of articular cartilage," Clinical Orthopaedics and Related Research, 1994, pp. 18-32, No. 303, J. B. Lippincott Company, USA.
Mankin, et al., "Clinical experience with allograft implantation," Clinical Orthopaedics and Related Research, 1983, pp. 69-86, No. 74, J. B. Lippincott Co., USA.
Matsusue, et al., "Arthroscopic Multiple Osteochondral Transplantation to the Chondral Defect in the Knee Associated with Anterior Cruciate Ligament Disruption," Arthroscopy: The Journal of Arthroscopic and Related Surgery, 1993, pp. 318-321, vol. 9, No. 3, Raven Press, Ltd., USA.
Maury, et al., "Twenty-five year chondrocyte viability in fresh osteochondral allograft. A Case Report," The Journal of Bone & Joint Surgery, 2007, pp. 159-165, vol. 89, Needham, MA, USA.
McPherson, et al., "Creep Behaviour of Osteochondral Grafts in Sheep," 39th Annual Meeting, Orthopaedic Research Society, 1993, p. 227, Alberta, Canada.
Meyers, Marvin, M.D., "Resurfacing of the Femoral Head with Fresh Osteochondral Allografts," Clinical Orthopaedics and Related Research, 1985, pp. 111-114, No. 197, San Diego, CA, USA.
Oakeshott, et al., "A Clinical and Histological Analysis of Failed Fresh Osteochondral Allografts," Clinical Orthopaedics and Related Research, 1988, pp. 283-294, No. 233, Ontario, Canada.
Outerbridge, R.E., "Joint surface transplants—a preliminary report," The Journal of the Western Pacific Orthopaedic Association, 1971, pp. 1-15, vol. VIII, No. 1, USA.
Pap, et al., "Arthroplasty of the Knee: Experimental and Clinical Experiences," The Journal of Bone & Joint Surgery, 1961, pp. 523-537, vol. 43-A, No. 4, Needham, MA, USA.
Rechenberg, et al., "Changes in subchondral bone in cartilage resurfacing—an experimental study in sheep using different types of osteochondral grafts," OsteoArthritis and Cartilage, 2003, pp. 265-277, vol. 11, Elsevier Science Ltd, Canada.
Rodrigo, et al., "Osteocartilaginous Allografts as Compared with Autografts in the Treatment of Knee Joint Osteocartilaginous Defects in Dogs," Clinical Orthopaedics and Related Research, 1978, pp. 342-349, No. 134, J.B. Lippincott Company, USA.
Roffman, Moshe, "Autogenous grafting for an osteochondral fracture of the femoral condyle," Acta Orthop Scand, 1995, pp. 571-572, vol. 66, No. 6, Sweden.
Schachar, et al., "The effect of Cryopreservative Agents on the Viability of Frozen Human Articular Cartilage," Canadian Orthopaedic Research Society, 1978, pp. 79-80, Canada.
Schachar, et al., "Fate of massive osteochondral allografts in a feline model," Osteochondral Allografts, Biology, Banking, and Clinical Applications, 1983, pp. 81-101, USA.
Schachar, et al., "Metabolic and biochemical status of articular cartilage following cryopreservation and transplantation: a rabbit model," Journal of Orthopaedic Research, 1992, pp. 603-609, vol. 10, Raven Press, New York, USA.
Shahgaldi, et al., "Repair of Cartilage Lesions Using Biological Implants," Journal of Bone & Joint Surgery, 1991, pp. 57-64, vol. 73-B, No. 1, England.
Shimizu, et al., "Bone resorption by isolated osteoclasts in living versus devitalized bone," Journal of Bone and Mineral Research, 1990, pp. 411-418, vol. 5, No. 4, Mary Ann Liebert, Inc., Boston, MA, USA.
Stevenson, et al., "The fate of articular cartilage after transplantation of fresh and cryopreserved tissue antigen-matched and mismatched osteochondral allografts in dogs," The Journal of Bone & Joint Surgery, 1989, pp. 1297-1307, vol. 71-A, No. 9, USA.
Toolan, et al., "Development of a novel osteochondral graft for cartilage repair," Novel Ostochondral Graft, 1998, pp. 244-250, John Wiley & Sons, Inc., USA.
Volkov, et al., "Use of Allogenous Articular Bone Implants as Substitutes for Autotransplants in Adult Patients," Clinical Orthopaedics and Related Research, 1976, No. 114, pp. 192-202.
Wada, et al., "Architectural remodeling in deep frozen meniscal allografts after total meniscectomy," Arthroscopy: The Journal of Arthroscopic and Related Surgery, 1998, pp. 250-257, vol. 14, No. 3, USA.
Wohl, et al., "Assessment of Bone Mechanical Integrity in Osteochondral Grafts," Orthopaedic Research Society, 1994, p. 526, Canada.
Yamashita, et al., "The Transplantation of an Autogeneic Osteochondral Fragment for Osteochondritis Dissecans of the Knee," Clinical Orthopaedics and Related Research, 1985, pp. 43-50, No. 201, Japan.
Garrett, John C, "Osteochondral Allografts", Instructional Course Lectures, vol. 42, (1993), 355-8.
Hurtig, M, et al., "Surgical and analytical techniques for assessment of transplanted articular cartilage: A pilot study", Twenty-ninth Annual Meeting of the Society for Cryobiology Ithaca, New York, USA, (1992), 732.
"U.S. Appl. No. 12/196,831, Final Office Action Mailed Apr. 12, 2012", 17 pgs.
Ehalt, W, "Bisherige Erfahrungen mit dem plastischen Ersatz von Gelenkknorpel aus der Knochenbank", Verh. Dtsch. Orthop. Ges. 43, (1955), 107-109.
Ehalt, W., et al., "Gelenkknorpel-Plastik", Langenbecks Arch. Kiln. Chir. 299, (1962), 768-774.
Ehalt, Walther M, "Grafting of joint-cartilage Bone-Blocks from the bank", VI. Congr. Soc. Internat. Chir. Orthop. Traumatol. S., (1954), 419-421.
Hangody, L, et al., "Autogenous osteochondral grafting in the knees of German Shepherd dogs: Radiographic and histological analysis", Hungarian Review of Sports Medicine 35, (1994), 117-123.
Hangody, L, et al., "Treatment of localized chondral and osteochondral defects in the knee by a new autogenous osteochondral grafting tenique", Hungarian Review of Sports Medicine 35, (1994), 241-246.
Hangody, Laszlo, et al., "Sülyos, körülírt térdízületi porckárosodás sebészi kezelésének új lehetosége (New alternative in the treatment of sever, localized cartilage damages in the knee joint)", Hungarian Journal of Traumatology and Orthopaedics 37, (1994), 237-242.
WO 93/15694, Multi-Phase Bioerodible Implant/Carrier and Method of Manufacturing and Using Same, Publication Date Aug. 19, 1993.
WO 96/24310, Multi-Stage Collagen-Based Template or Implant for Use in the Repair of Cartilage Lesions, Publication Date Aug. 15, 1996.
WO 96/24302, Surgical Implantation of Cartilage Repair Unit, Publication Date Aug. 15, 1996.
WO 96/27333, Apparatus and Methods for Articular Cartilage Defect Repair, Publication Date Sep. 12, 1996.
WO 97/46665, Method for Making Cartilage and Implants, Publication Date Dec. 11, 1997.
WO 98/56317, Joint Prosthesis, Publication Date Dec. 17, 1998.

* cited by examiner

PREPARATION FOR REPAIRING CARTILAGE DEFECTS OR CARTILAGE/BONE DEFECTS IN HUMAN OR ANIMAL JOINTS

Matter enclosed in heavy brackets [ ] appears in the original patent but forms no part of this reissue specification; matter printed in italics indicates the additions made by reissue.

BACKGROUND OF THE INVENTION

1. Field of the Invention

The present invention lies in the field of medical technology and generally relates to a device for repairing cartilage defects and/or cartilage/bone defects in human or animal joints. More specifically, the device serves to repair defects in the cartilage layer, which in joints covers the bone surface, or of defects that concern this articular cartilage layer and also bone tissue lying thereunder.

2. Description of Related Art

Damage to articular cartilage by way of injuries or involution caused by aging or disease is particularly common in humans. Very often such damage also takes its toll on the bone tissue lying below the articular cartilage. The degree of damage to articular cartilage defects and/or cartilage/bone defects is determined with the help of the Outerbridge scale, with the following categories: superficial fraying (approx. 10% of all cases), cartilage fissure (approx. 28%), fissure down to the bone (approx. 41%), damage involving cartilage and bone (approx. 19%) and other damage such as osteochondritis dissecans and joint fracture (approx. 2% of all detected cases).

Vital cartilage tissue contains living cells by way of whose activity the specific intercellular cartilage matrix is built up during adolescence. However, it contains very little vascularization in the fully grown condition and, therefore, has a very limited regeneration capability. This means that cartilage defects or cartilage bone defects, in particular those defects concerning a relatively large cartilage surface, do not heal by themselves and therefore must be repaired by surgery (Mankin H J: The response of articular cartilage to mechanical injury, Journal of Bone and Joint Surgery (Am) 64A (1982) March: pages 460-466).

For repairing the named defects it is, for example, suggested to implant devices comprising the tissue to be repaired or a perform of this tissue. Such devices are cylindrical and comprise a cartilage layer on one end face. For implantation a pocket-hole shaped opening or bore is produced in the region of the defect to be repaired and the device is positioned in the bore such that the cartilage layer of the implant faces towards the outside. The bore, independently of the depth of the defect, extends into the healthy bone tissue. The device has a somewhat larger diameter than the bore and the same axial length. Therefore, after implantation there is a radial tension (press fit) between native tissue and the implanted device by way of which the implant is held in the bore. The cartilage surface of the implant is flush with the surrounding native cartilage surface. The devices have, according to the size of the defect, a diameter of 4 to 10 mm (e.g. 5.4 mm for the device and 5.3 mm for the bore) and lengths of approx. 10 to 20 mm.

For larger defects it is suggested to implant a plurality of such cylindrical devices in the defect region in a mosaic manner and to fill out the intermediate spaces between the implants with a suitable material.

The cylindrical devices are for example autologous (autotransplants). For the repair of an articular cartilage defect concerning a heavily loaded location of a joint, a suitable tissue piece is harvested, for example, from a less loaded location of the same joint and is transplanted into a bore created at the defect location using a hollow drill (Hangody L et al.: Mosaicplasty for the treatment of articular cartilage defects: application in clinical practice. Orthopedics 1998 Jul., 21(7):751-6).

The cylindrical devices may also originate from a suitable donor (homologous transplants). Also known are suitable heterologue implants or xenotransplants which before implantation are suitably treated, e.g. photo-oxidized (as described in the publication EP-0768332 of Sulzer Innotec), for preventing immune-reaction after implantation or for minimizing such immuno-reaction (immunological deactivation). Such implants are, for example, removed from shoulder joints of slaughtered cattle and have the advantage of being available in much larger numbers than autologous or homologous transplants and of causing no secondary defects on harvesting, which secondary defects must be repaired and lead to new difficulties.

In the publication WO-97/46665 (Sulzer Orthopedics) a suitable device is described of which the bone part consists of bone replacement material and the end-face cartilage layer is grown onto it in vitro from autologous chondrocytes.

In all mentioned devices being made from natural tissue there is a natural connection or coalescence between the end-face cartilage layer and the bone part and there is an outermost bone region (subchondral bone plate) in which the bone tissue is more compact than in other bone regions. The mentioned, partly artificial implants also show the coalescence of cartilage layer and bone part and the artificial bone part is advantageously equipped with a more compact, that is to say less porous, outer layer which serves the cartilage layer as an underlay.

An important function of the subchondral bone plate or an artificial imitation thereof is evidently the prevention of vascularisation of the cartilage layer proceeding from the bone tissue, which would lead to ossification of the cartilage. In addition the subchondral bone plate having a higher density than the inner bone tissue represents a region of higher mechanical strength.

With the devices as mentioned above it is attempted to achieve the following targets:

- The bone part of the device is to allow solid anchoring of the implant by way of a press fit, in a manner such that the implant requires no further fastening means interfering with healthy cartilage regions.
- The coalescence of cartilage layer and bone part in the device is to give the implant stability so that the cartilage layer cannot be detached and removed from the defect location, even if the joint is not immobilized after implantation.
- The cartilage layer of the device Is to have a mechanical strength and elasticity such that the repair location may be fully loaded directly after implantation.
- The cartilage layer is to form a zone in which conditions suitable for the implanted cells or for cells migrating into it after implantation prevail, such that the cell can produce or maintain a fully functional cartilage tissue. This is also to be supported by the subchondral bone plate which separates the cartilage layer from the bone part and which helps to prevent vascularisation proceeding from the bone part.
- The bone part is to represent a zone in which conditions suitable for the implanted cells or for cells migrating into it after implantation prevail, such that they can produce or maintain a fully functional bone tissue.

New trials in which artificially produced defects in joints of sheep have been repaired with auto-transplants, homo-transplants or with hetero-transplants (from cattle tissue) in the previously mentioned manner, show that the healing process after implantation does not proceed as expected.

In particular, it has been shown that the bone part of the implants is not integrated in the native tissue or replaced gradually by new reparative tissue, but that the bone part of the implant undergoes a transformation process with essentially three successive phases. In a first step bone osteoclastic cells (osteoclasts) are stimulated and the implanted bone starts to be resorbed. This first phase is already clearly visible six to eight weeks after implantation. A hollow space (cyst) then arises in the implant and is filled with connective tissue. This second phase reaches a climax after approximately six weeks. In the third and last phase bone-forming cells (osteoblasts) are attracted which convert the connective tissue to bone. This conversion process is concluded after about twelve months. Then the newly created bone structure is so well adapted that the original border between the implant and the surrounding bone tissue can hardly be perceived anymore.

Due to the described, three-phase transformation process comprising a middle phase in which the cartilage layer of the implant is not carried by the bone part capable to do so but by a mechanically inferior cyst, there exists a high risk that the cartilage layer is pressed into this cyst where it can neither fulfill its mechanical nor its biological function and from where it cannot be displaced during the following phases of the healing process. This risk significantly reduces the chances of healing success. Healing with a badly positioned cartilage layer causes negative after-effects.

It is surprising that the trials show the cyst formation at the location of the bone part of an implant in a middle phase of the healing process not only for homologous and heterologous implants, but in particular also for auto-transplants. The initial resorption of the implanted bone tissue does not therefore appear to be an immuno-reaction in which implanted vital material is recognized as foreign and is therefore resorbed. It would appear that it is rather a reaction to implanted, dead material. This means that by cutting off the natural blood supply on harvesting the implant even when harvesting it from viable tissue and even when it is implanted directly after harvesting, the bone tissue loses its viability. In any case, the bone part of the implant is resorbed and is rebuilt only after substantially complete resorption.

SUMMARY OF THE INVENTION

It is an object of the invention to provide a device for repairing cartilage defects or cartilage/bone defects in human or animal joints, which device prevents the above described risk of an implanted cartilage layer to sink into the region of the native bone tissue. The device according to the invention allows production and implantation in a manner equally simple as for known devices comprising a bone part and a cartilage layer calescent with the bone part.

The device according to the invention that serves for repairing cartilage defects or cartilage/bone defects in human or animal joints, is based on the finding that the subchondral bone plate is evidently present essentially unchanged when the bone part is completely or to a great extent replaced by connective tissue in the middle critical phase of the above described healing process. This is probably attributed to the fact that the subchondral bone plate, on account of its higher density, is resorbed significantly more slowly than the inner regions of the bone part. Since this subchondral bone plate is mechanically sufficiently stable, sinking of the cartilage layer grown thereon into a cyst underneath is prevented when the subchondral bone plate is supported not only by implanted bone material but in addition by material with different resorption properties such that during the critical healing phase it remains non-displaceable. When the subchondral bone plate of the implant is resorbed after the critical phase, that is to say at a point in time in which the loading capability of the inner implant region is restored again, this will not greatly influence the healing process.

Improved support of the implanted device during the critical healing phase can be realized in essentially two ways.

On the one hand the implant may be formed such that the cartilage layer and the subchondral bone plate of the device have a larger cross section than the bone part. Such a device is implanted into a two stage bore such that the subchondral bone plate of the device is not only supported on the bone part of the implant but also on healthy bone tissue next to the bore set up for repair.

On the other hand the bone part of the device may be equipped with columns having a reduced resorbability. These columns extend axially through the bone part up to the subchondral bone plate. The resorbability of the columns relative to the resorbability of the bone part regions between the columns may be reduced by way of a suitable chemical treatment or by way of producing axial bores in the bone part of the device and filling these with an artificial material more resistant to resorption.

BRIEF DESCRIPTION OF THE DRAWINGS

These and further features of the invention will be apparent with reference to the following description and drawings, wherein.

DETAILED DESCRIPTION OF THE PREFERRED EMBODIMENTS

Figure 1:
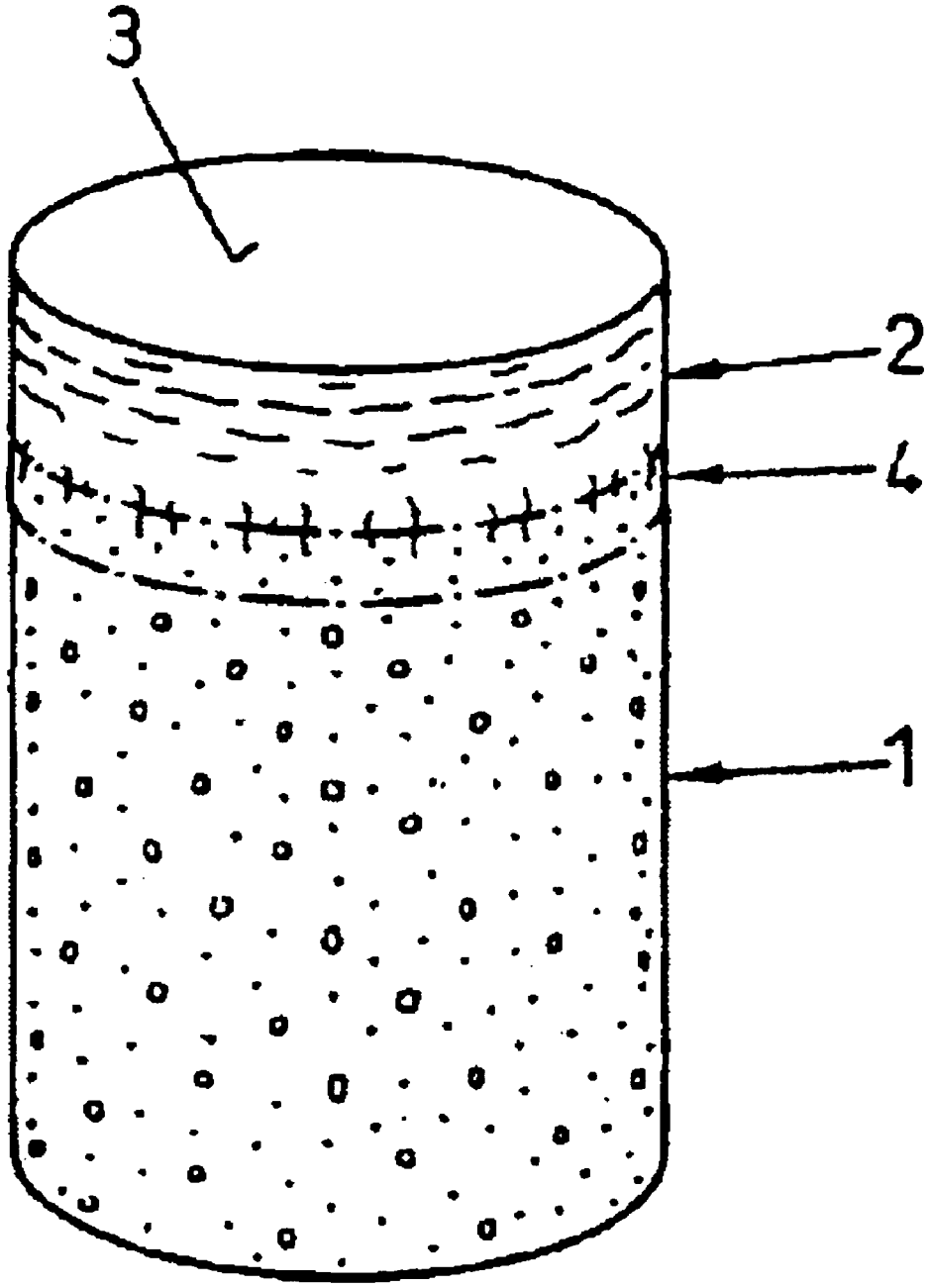
FIG. 1 PRIOR ART
FIG. 1 shows a known cylindrical device for repairing cartilage defects or cartilage/bone defects in human or animal joints.

FIG. 1 shows a device as used according to the state of the art for repairing cartilage defects or cartilage/bone defects in human or animal joints. The device is cylindrical, advantageously with a circular cross section, and comprises a bone part 1 and cartilage layer 2 grown on one end face onto the bone part 1. The cartilage layer 2 forms a cartilage surface 3. Between the bone part 1 and the cartilage layer 2 there extends a subchondral bone plate 4. The transitions from the bone part 1 to the subchondral bone plate 4 and from the subchondral bone plate 4 to the cartilage layer 2 are not visible as lines, as is shown in FIG. 1 in a simplified manner, but they are natural, rather continuous transitions.

As already mentioned a device as shown in FIG. 1, is harvested from advantageously vital tissue using a hollow drill and is implanted if possible immediately after harvesting (auto-transplants and homo-transplants), or it is removed from joints of slaughtered animals (e.g. from shoulder joints of slaughtered cattle) and before implantation is subjected to a treatment for immunological deactivation.

Figure 2:
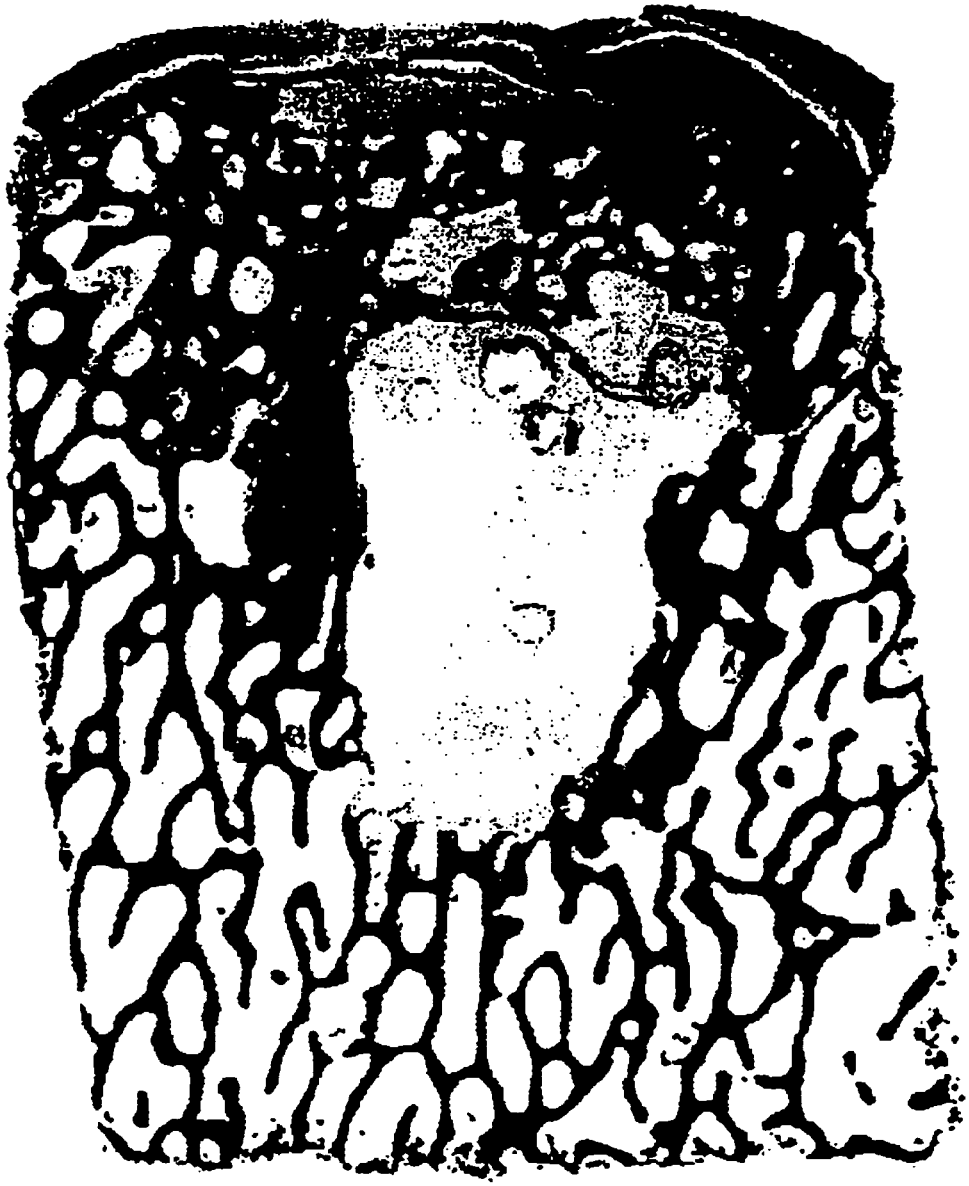
FIGS. 2 to 4 show tissue sections through cartilage/bone defects in a sheep's joint being repaired with a device according to FIG. 1, at various points in time after the implantation.
Figure 3:
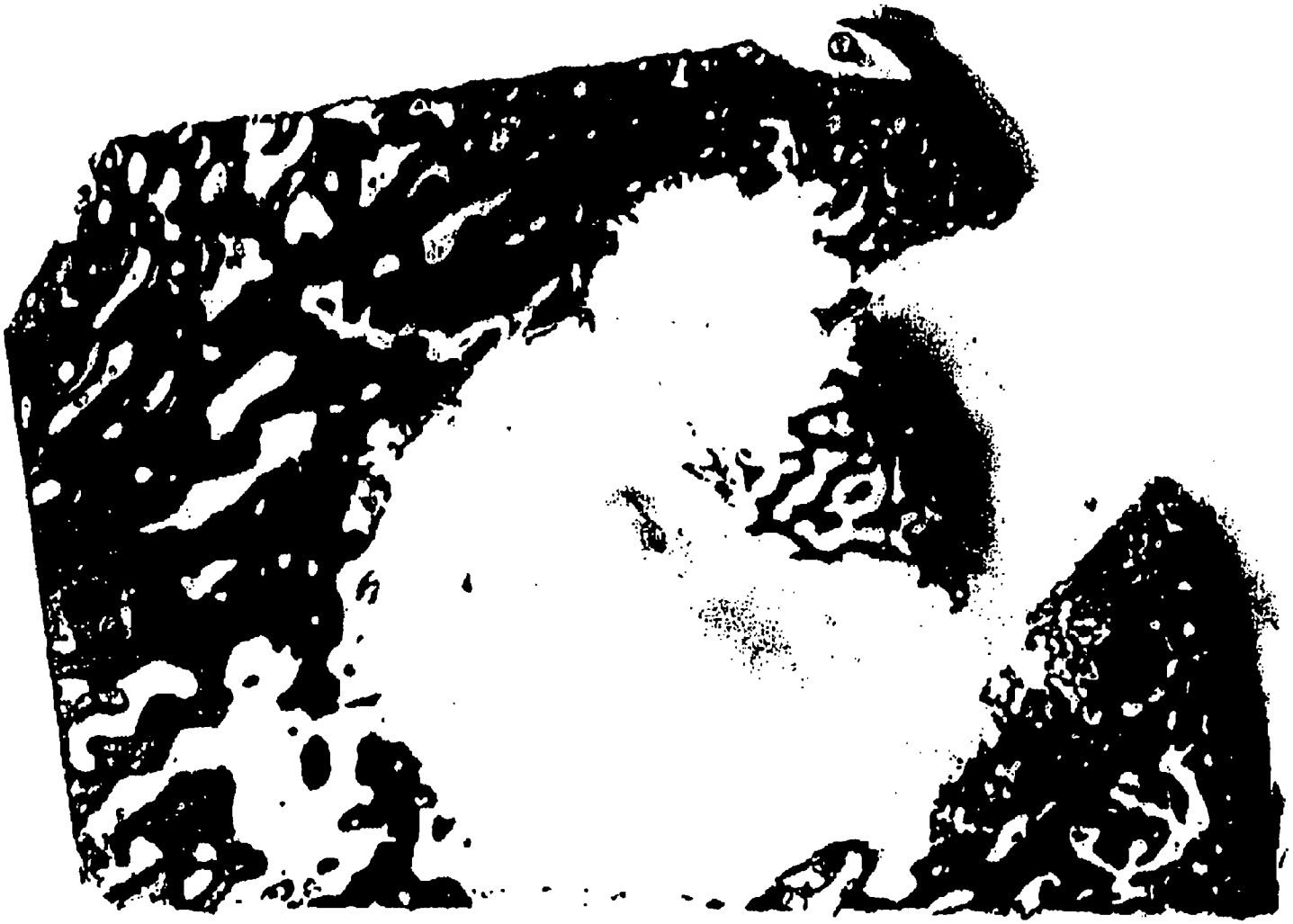
Figure 4:
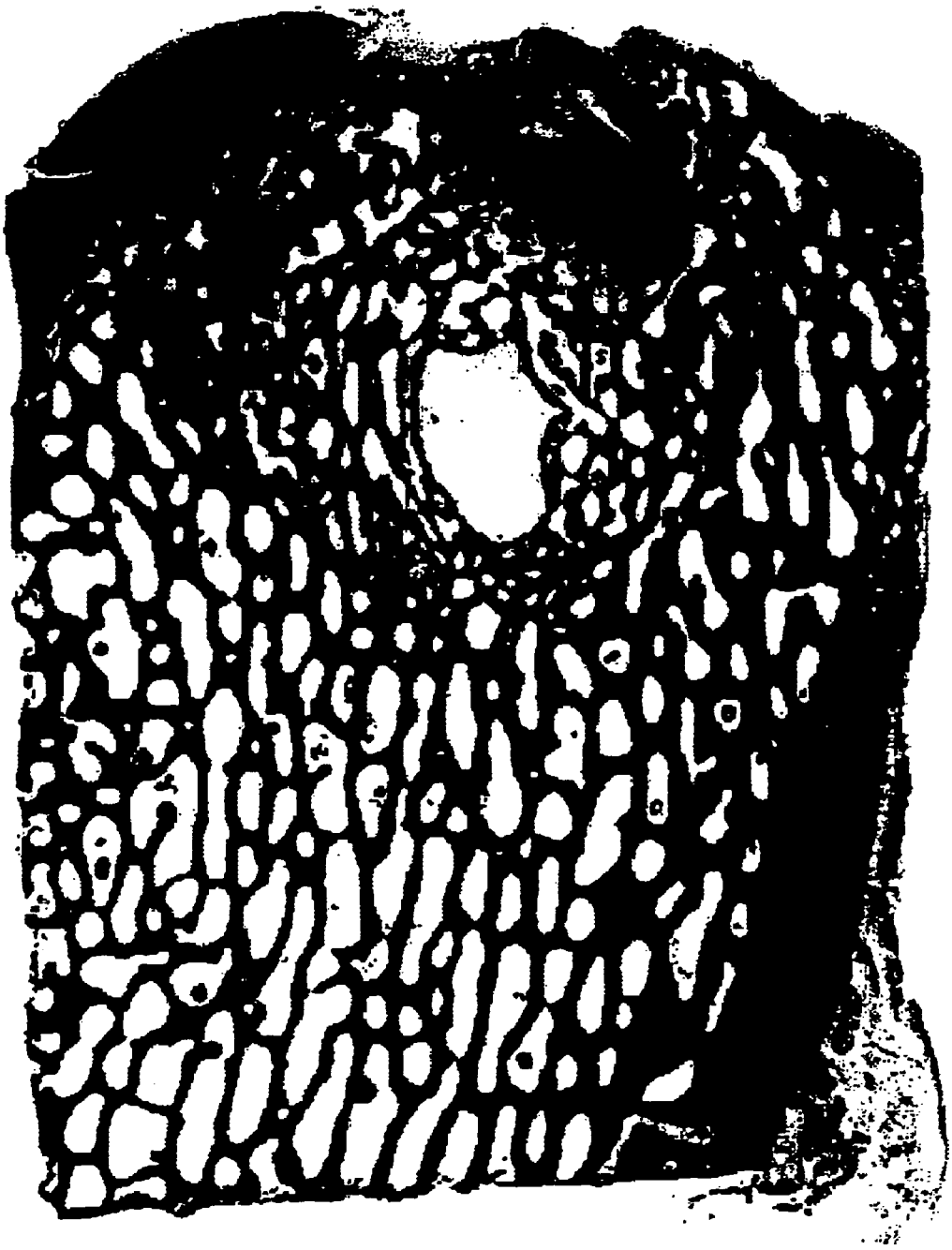

FIGS. 2 to 4 illustrate the trials with implants according to FIG. 1 in sheep's joints which have already been discussed further above and they further illustrate the risk connected with such implants. The drawings show tissue sections through repair locations parallel to the axis of the implant, which in the enlarged drawings projects from the cartilage surface (top side of the Fig.) about 7 cm into the bone tissue. FIGS. 2 and 3 show implant sites six months after implantation with cyst-like cavities in the bone tissue. FIG. 2 shows a case in which the cartilage layer is still positioned at its original location, in FIG. 3 it has sunk into the cyst space.

As is evident from FIGS. 2 and 3, in the critical time period in which at the location of the implanted bone part there is a cyst-like cavity, the subchondral bone plate of the implant is substantially unchanged. This finding is attributed to the higher density of the subchondral bone plate relative to the inner bone tissue and therefore a reduced resorbability. The subchondral bone plate of the implant has evidently different resorption properties than have inner regions of the bone part.

The trials were carried out with auto-transplants and with hetero-transplants. For seven treated animals the repair locations were examined after six months and in ten cases (five animals) cartilage layers were found to be displaced into the cyst cavity, in four cases (two animals) the cartilage layers had remained in place. In none of the cases the cartilage layer was lost into the joint space.

The results of the trials show that evidently adhesion between the cyst and the implanted cartilage layer or the subchondral bone plate respectively is sufficient for preventing removal of the cartilage layer from the repair location, but that the loading capability of the cyst is not sufficient for preventing the cartilage layer from being displaced towards the inside.

FIG. 4 shows a similar repair location twelve months after implantation. An unevenness in the cartilage surface caused by the sinking-in of the implanted cartilage layer is clearly visible. In the series of trials repair locations on seven treated animals were examined after twelve months and in two cases unevennesses in the cartilage surface as shown in FIG. 4 were found. In the remaining cases the cartilage surface in the repair region was even.

Figure 5:
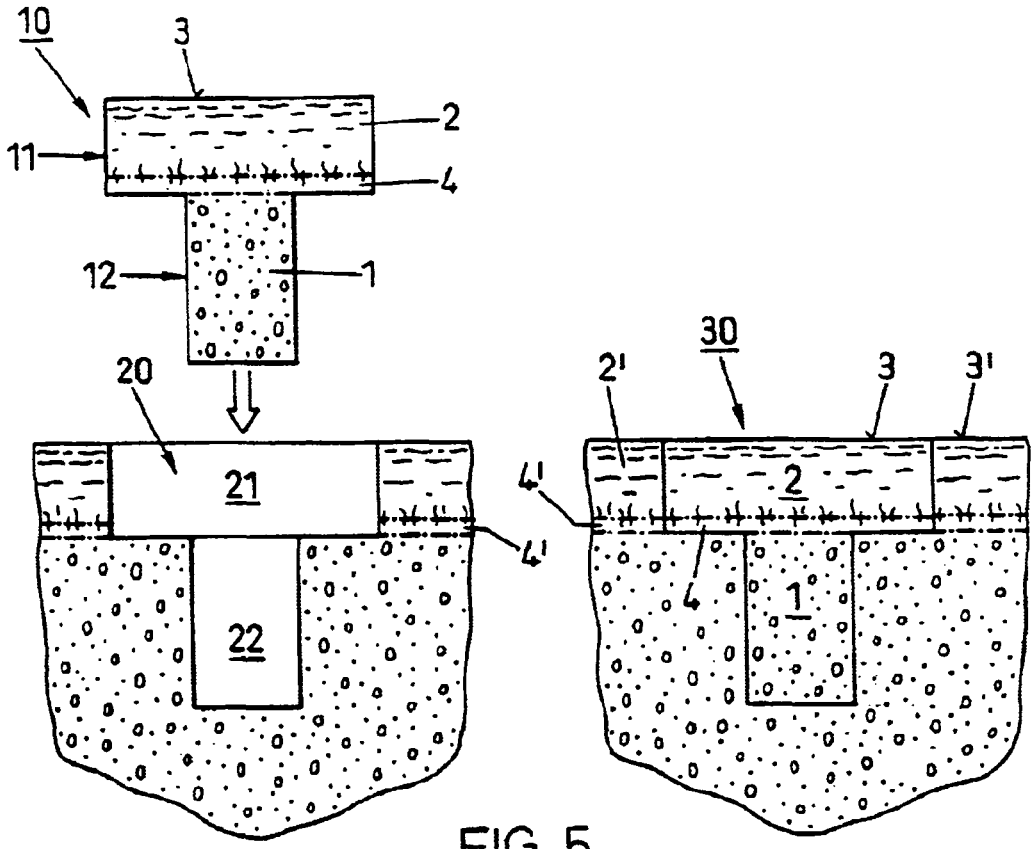
FIG. 5 shows a schema of the repair of a cartilage defect with the help of a preferred embodiment of the device according to the invention (section along the axis of the device or the bore)

FIG. 5 shows a preferred embodiment of the device according to the invention for repairing cartilage or cartilage/bone defects in human or animal joints. It shows the device 10, the opening or bore 20 to be set up for implantation of the device, and the device inserted in the opening, the implanted device 30 (section along the axis of the device 10 or of the opening 20).

The device 10 has in the same manner as the device of FIG. 1 a bone part 1, and on one end face of this, a cartilage layer 2 forming a cartilage surface 3. In the transition region between the bone part 1 and the cartilage layer 2 there is a subchondral bone plate 4. The device has a top part 11 with a larger cross section and a bottom part 12 with a smaller cross section. The top part 11 comprises essentially the cartilage layer 1 and the subchondral bone plate 4, the bottom part 12 essentially corresponds to the bone part 1. The bottom part 12 has advantageously (but not necessarily) the shape of a circular cylinder or steep angle truncated circular cone and the top part 11 projects on all sides beyond the bone part 1 and is for example likewise circularly cylindrical.

Auto-transplants and transplants of living donors have advantageously cylindrical top parts since such devices should cause as small as possible harvesting sites. Devices produced from the tissue of slaughtered animals (advantageously cattle or pigs) may without causing problems have head parts with any shape of cartilage surface. This is so due to the easy availability of the material allowing production of wastage. But also in this case it is advantageous to form the bottom part in a manner such that the opening to be made for implantation can be created with a simple tool, for example with a drill.

A device 10 with circular cross section at least in the foot region is for example manufactured from a suitable cylindrical device in that the bone part is accordingly machined. This machining may be carried out with a tool In which the cylindrical device is positioned and in which blades are activated to reduce the cross section of the device 10 to a predetermined extent at a predetermined or adjustable distance from the cartilage surface.

The opening or bore 20 which is to be created in a defect region for implanting the device 10 has an outer region 21 adapted to the top part 11 of the device 10 and having a depth down to the region of the native subchondral bone plate 4', and an inner region 22 adapted to the bottom part of the device, whose depth is adapted to the shape of the defect to be repaired and to the length of the device to be implanted. The dimensions of the device 10 and of the bore 20 are to allow for a press fit in the region of the top part as well as in the region of the bottom part.

A bore 20 as shown in FIG. 5 is for example created with a tool comprising a blade with a circular cutting edge and two drills or hollow drills movable relative to the cutting edge in an axially limited manner. The tool is positioned on the defect location and the blade is pressed down to the subchondral bone plate. Then the outer region 21 is drilled out with the first drill, which may be moved beyond the cutting edge of the blade by the thickness of the subchondral bone plate, and whose diameter corresponds essentially to the inner diameter of the blade. Afterwards the inner region 22 is drilled out using the second drill, wherein the drilling depth relative to the cutting edge or relative to the end position of the first drill may be adjusted.

FIG. 5 shows on the right hand side the implanted device 30, that is to say the device 10 implanted in the bore 20. The implanted device 30 comprises a cartilage surface 3 flush with the native cartilage surface 3' and a subchondral bone plate 4 roughly flush with the native subchondral bone plate 4'. The subchondral bone plate 4 of the implant is evidently supported on the one hand on the bone part 1 of the implant and on the other hand on native bone tissue directly below the native, subchondral bone plate 4' or in its region. For achieving a press fit for the head region 1 of the implant, it is advantageous to dimension the outer region 21 of the bore with a depth such that the subchondral bone plate 4 of the implant is not only radially supported on native cartilage tissue 3' but also on native bone tissue (subchondral bone plate 4'), as this is shown in FIG. 5.

For implanting a device in a bore, as shown by FIG. 5, a tool is used. The tool comprises, for example, a sleeve and a plunger axially movable in the sleeve. The sleeve has an inner cross section that corresponds to the cross section of the top part of the device to be implanted. The plunger advantageously has a cross section roughly equal to the top part; it is longer than the sleeve and has a channel that begins on the end face of the plunger and is connectable to a suction conduit in the region of the other end of the plunger.

For implantation, the end face of the plunger with the channel opening is pushed into the sleeve and using the suction force, a device to be implanted is drawn into the sleeve. Then the sleeve together with the plunger and the device suctioned thereon is positioned over the prepared bore and the device is pressed into the bore with the help of the plunger and where appropriate using a hammer.

It has been shown that resorption of the bone part of an implanted device also affects regions of the native bone tissue bordering the implant. For this reason it is recommended to dimension the protrusion of the top part to about 1 to 2 mm (e.g., bone part with a diameter of approximately 3 mm, top part with a diameter of 5 to 6 mm).

Figure 6:
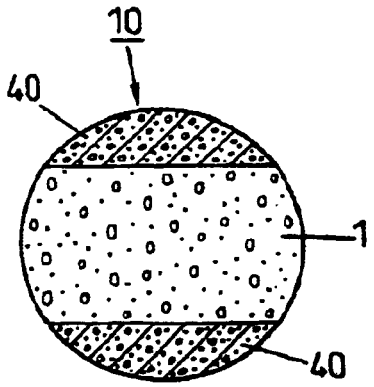
FIGS. 6 and 7 show two further exemplary embodiments of the device according to the invention, in cross section; and, FIGS. 8 and 9 show sections through a cartilage defect (FIG. 8) and through a cartilage/bone defect (FIG. 9), both repaired in a mosaic manner with a plurality of inventive devices according to FIG. 5.
Figure 7:
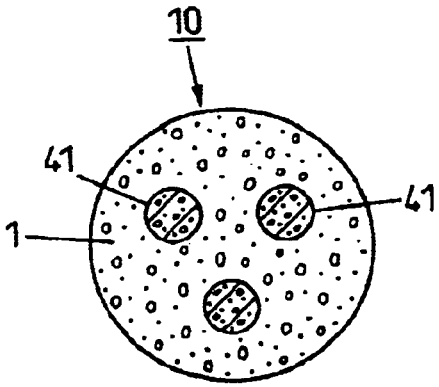

FIGS. 6 and 7 show two further exemplary embodiments of the device according to the invention. These are not based on the idea of supporting the subchondral bone plate of the device on native bone tissue as is shown in FIG. 5, but rather on the idea of establishing in the bone part at least one column having a resorbability different from the resorbability of the rest of the bone material in the bone part 1 such that at the point in time in which the remaining bone tissue of the bone part is resorbed, the columns bear the subchondral bone plate and the cartilage layer grown onto it and, therefore, prevent the cartilage from sinking into the cyst region.

FIGS. 6 and 7 are cross sections through bone parts 1 of devices according to the invention. These devices are, for example, cylindrical and in the bone part have axially extending columns consisting of a material that is resorbed more slowly than the bone material of the regions between the columns. The columns are, for example, arranged on the surface of the bone part (surface columns 40 in FIG. 6) and are produced by a suitable treatment of the bone material, or they are located in the inside of the bone part (inner columns 41 in FIG. 7) and are produced by creating bores and filling the bores with a suitable material. In both cases, the columns extend up to at least the subchondral bone plate.

For local reduction of the resorbability of bone material, a treatment with [biphosphonate] *bisphosphonate* may be used [("Biophosphonates] (*"Bisphosphonates* in Bone Disease" Herbert Fleisch, the Parthenon Publishing Group, New York and London 1995). As a resorbable material for filling bores for example a hydroxy apatite ceramic material may be used.

Figure 8:
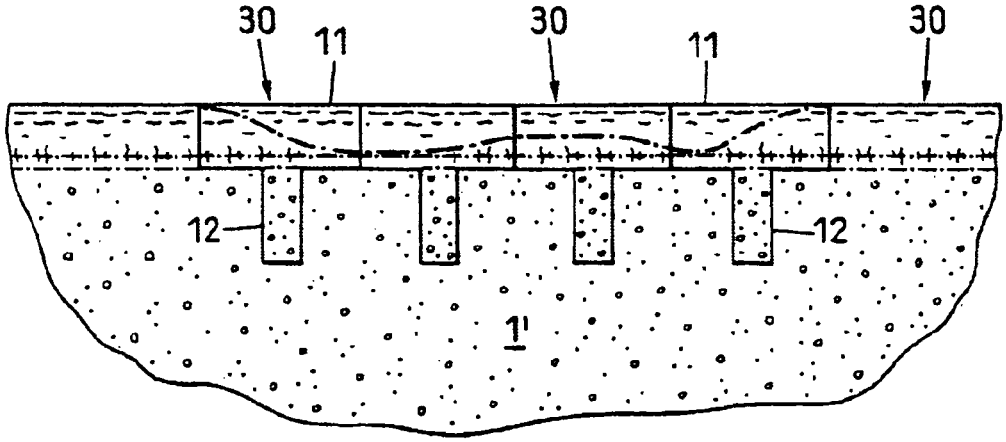
Figure 9:
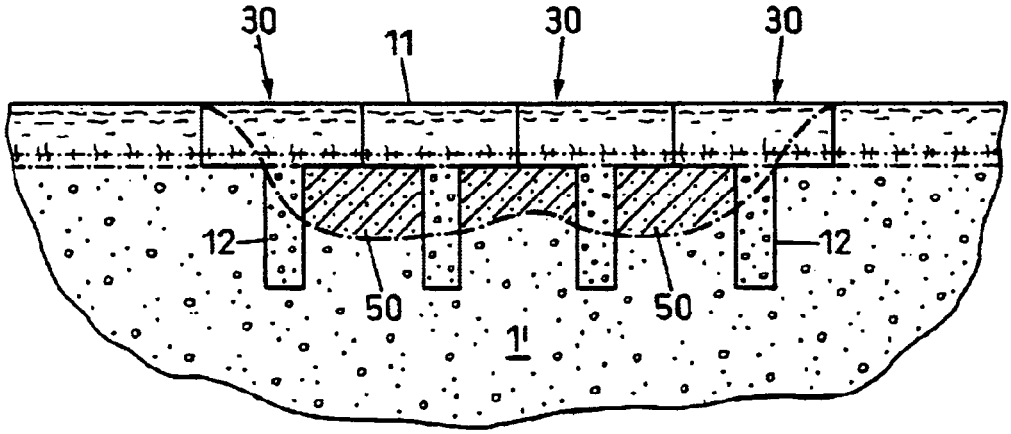

FIGS. 8 and 9 show a cartilage defect (FIG. 8) and a cartilage/bone defect (FIG. 9) with dimensions of the type such that they cannot be repaired with a single implant. The defects are indicated with dot-dashed lines. The repair consists of a mosaic-like arrangement of devices according to the invention, as shown in FIG. 5.

As mentioned above, it is possible also to use implants according to the state of the art (FIG. 1) for such mosaic-like arrangements for repairing larger defects. The cylindrical devices are implanted as close as possible next to one another, wherein on the one hand there will be gaps in the cartilage layer and on the other hand the regions of native bone tissue between the bone parts of the implants will be very narrow. It has been shown that the chances of healing of such repairs are better in edge regions than in middle regions. One may presume that this is due, on the one hand, to the deficient compactness of the freshly created cartilage layer and, on the other hand, to the deficient repair ability of the greatly reduced native bone tissue between the implants.

FIG. 8 shows that the implants 30 with the top parts 11 also in a mosaic repair allow supporting of the cartilage layer and the subchondral bone plate of the implants on native bone tissue 1' and thereby counteract a sinking of the cartilage layer in a critical healing phase. It is also evident that the regions of native bone tissue 1' between the bottom parts 12 of the implants are wider than the case would be with cylindrical implants. This means that the healing chances are improved in contrast to the state of the art. It is also evident that the cartilage surface may be formed essentially without interruption over the complete defect region if the shape of the top parts is accordingly selected (e.g. square, rectangular, triangular, or hexagonal).

FIG. 9 shows a cartilage/bone defect (indicated with a dot/dashed line) that has been repaired with a plurality of devices according to FIG. 5. The bottom parts 12 of the implants 30 extend into healthy bone tissue 1'. Locations 50 where bone material is missing or damaged bone material has been removed are filled out with a suitable material (for example tricalcium phosphate or hydraulic bone cement). This material is to be selected such that it is resorbed either before or after the bottom parts 12 of the implants 30 and so that, in the critical phase of the healing process in which the bone parts of the implants are resorbed and not yet replaced, it can support the cartilage layers and prevent them from sinking. Advantageously the filling material has a mechanical strength sufficient for being drilled straight after being filled into the defect.

The additional advantages described for the repair according to FIG. 8 apply also to the repair according to FIG. 9.

What is claimed is:

1. A device [(10)] for repairing cartilage defects or cartilage/bone defects in human or animal joints, said device comprising a bone part [(11)], a cartilage layer [(2)] grown onto the bone part [(1)] and forming a cartilage surface [(3)], and a subchondral bone plate [(4)] or an imitation of a such a bone plate in a transition region between the bone part [(1)] and the cartilage layer [(2)], said device being implantable into an opening or a bore [(20)] set up in a defective ,region such that the bone part is adapted to be anchored in the healthy bone tissue and the cartilage surface [(3)] is flush with a native cartilage surface [(3')], wherein for supporting the subchondral bone plate [(4)] and the cartilage layer [(2)] of the implanted device on at least two materials with differing resorbabilities, a cross-section of the bone part [(1)] is smaller than a cross section of the subchondral bone plate [(4)] and the cartilage layer [(2)] or the bone part has column regions [(40, 41)] that extend to the subchondral bone plate [(4)] and have a resorbability different from a resorbability of the regions between the column regions.

2. The device according to claim 1, further comprising a top part [(11)] and a bottom part [(12)], wherein the top part [(11)] substantially comprises the cartilage layer [(2)] and the subchondral bone plate [(4)], and the bottom part [(12)] substantially corresponds to the bone part and wherein the subchondral bone plate [(4)] is larger than a cross section parallel to the subchondral bone plate through the bottom part [(12)] such that the subchondral bone plate [(4)] of the implanted device [(30)] is supported on native bone tissue.

3. The device according to claim 2, wherein the top part [(11)] and the bottom part [(12)] are coaxial circular cylinders.

4. The device according to claim 2, wherein the bottom part [(12)] is a circular cylinder and the top part [(11)] has a square, rectangular, triangular or hexagonal cartilage surface [(3)].

5. The device according to claim 1, wherein the column regions [(40, 41)] extend perpendicular to the subchondral bone plate [(4)] through the bone part [(1)] up to the subchondral bone plate [(4)], and wherein the column regions [(40, 41)] and regions between the column regions have different resorbabilities.

6. The device according to claim 5, wherein the device is essentially cylindrical and the cartilage layer [(3)] is arranged on one of its end faces.

7. The device according to claim 5, wherein a resorption behavior of the column regions [(40)] is altered with respect to a resorption behavior of the regions between the column regions by way of chemical treatment.

8. The device according to claim 7, wherein the column regions [(40)] consist of bone issue treated with [biphosphonate] *bisphosphonate*.

9. The device according to claim 1, wherein the column regions [(41)] consist of a bone replacement material filled into corresponding axial bores.

10. The device according to claim 1, wherein said device is made of autologous tissue.

11. The device according to claim 1, wherein said device is made of homologous or heterologous, immunologically deactivated tissue.

12. The device according to claim 11, wherein said device is made of tissue that is immunologically deactivated by way of photo-oxidation.

13. The device according to claim 11, wherein said device consists of tissue removed from slaughtered animals.

14. The device according to claim 13, wherein the tissue is removed from cattle or pig's joints.

15. A method for repairing cartilage defects or cartilage/bone defects in human or animal joints using a device [(10)] according to claim 2, comprising the steps of producing in the defect region an opening or bore [(20)] extending into healthy bone material and implanting the device [(10)] in the opening or bore, wherein the opening [(20)] comprises an outer region [(21)] and an inner region [(22)], a cross section of the outer region [(21)] is larger than a cross section of the inner region [(22)] and wherein the opening [(20)] is adapted, relative to the device [(10)], such that the device is implantable with a press fit and the cartilage surface [(3)] of the implanted device [(30)] is flush with the native cartilage surface [(3')].

16. The method according to claim 15, wherein a transition between the outer region [(21)] and the inner region [(22)] lies directly below the native subchondral bone plate [(4')].

17. The method according to claim 15, wherein the opening [(20)] is produced by drilling.

18. The method according to claim 15, wherein, for repairing larger defects, a plurality of devices are implanted in a mosaic-like manner, wherein positions for openings or bores [(2)] and the shape and size of top parts [(11)] of the devices [(10)] are coordinated to one another such that a cartilage surface [(3, 3')] essentially without interruption is achieved.

19. The method according to claim 18, wherein missing bone material between the openings is replaced with a bone replacement material having a resorbability that is different from the resorbability of the bone parts [(1)] of the devices [(10)].

*20. A device for repairing cartilage defects or cartilage/bone defects in human or animal joints, said device comprising a bone part, a cartilage layer grown onto the bone part and forming a cartilage surface, and a subchondral bone plate or an imitation of a such a bone plate in a transition region between the bone part and the cartilage layer, wherein: (a) resorbability of the bone part is faster than resorbability of the subchondral bone plate or an imitation of a such a bone plate; (b) the bone part of the device comprises columns that have reduced resorbability relative to the rest of the bone part; and (c) the columns extend axially through the bone part up to the subchondral bone plate.*

*21. The device of claim 20, wherein the subchondral bone plate or an imitation of such a bone plate protrudes on all sides from the bone part.*

*22. The device of claim 21, wherein the subchondral bone plate or an imitation of such a bone plate has the form of a circular cylinder which is arranged coaxial to the bone part.*

*23. The device of claim 21, wherein the cartilage layer forms a square, rectangular, triangular, or hexagonal cartilage surface.*

*24. The device of claim 20, wherein the bone part and the subchondral bone plate or an imitation of a such a bone plate comprise a bone material or a bone substituted material and at least part of the material of the subchondral bone plate or an imitation of a such a bone plate is of a higher density than the material of the bone part.*

*25. The device of claim 20, wherein the device comprises autologous tissue.*

*26. The device of claim 20, wherein the device comprises homologous or heterologous, immunologically deactivated tissue.*

*27. The device of claim 26, wherein the device comprises tissue that is deactivated by photo-oxidation.*

*28. The device of claim 26, wherein the device comprises tissue removed from at least one slaughtered animal.*

*29. The device of claim 28, wherein the tissue is removed from a cattle or pig joint.*

*30. The device of claim 20, wherein the resorbability of the columns has been reduced by chemical treatment.*

*31. The device of claim 30, wherein the chemical treatment comprises treatment with bisphosphonate.*

*32. The device of claim 20, wherein the columns comprise axial bores in the bone part that have been filled with a material that is more resistant to resorption than the rest of the bone part.*

*33. A device for repairing cartilage defects or cartilage/bone defects in human or animal joints, said device comprising a bone part, a cartilage layer grown onto the bone part and forming a cartilage surface, and a subchondral bone plate or an imitation of a such a bone plate in a transition region between the bone part and the cartilage layer, wherein the device is adapted to be implanted into a bore formed in or near a defect region of a human or animal joint, and wherein the bone part comprises at least one column having a resorbability different from the resorbability of the rest of the bone part.*

*34. The device of claim 33, wherein the at least one column is adapted to bear the subchondral bone plate after the device has been implanted in the bore and the rest of the bone part has been resorbed.*

* * * * *